Jan. 16, 1962 G. A. REID Plant Pat. 2,122
AZALEA PLANT
Filed Dec. 20, 1960
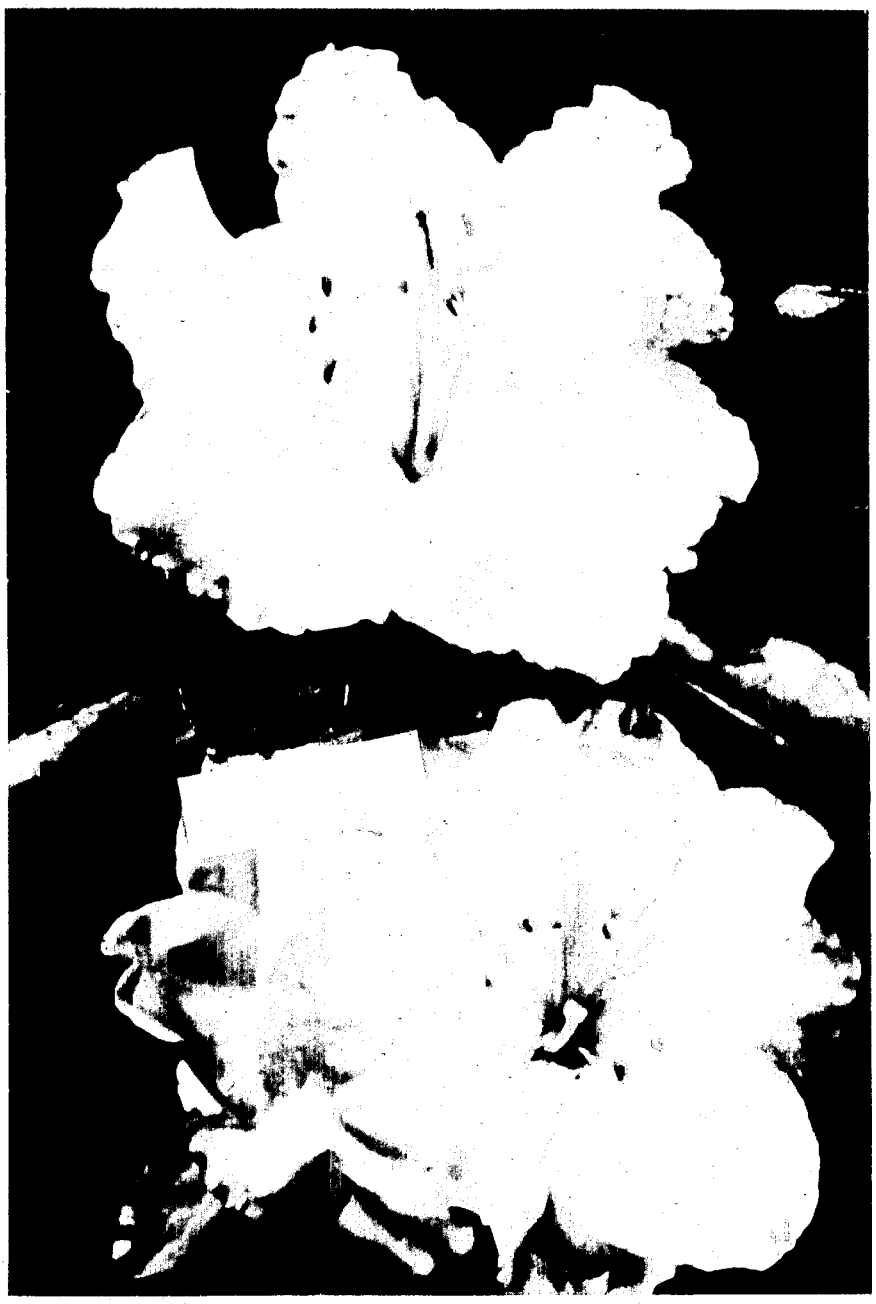
INVENTOR
George Albert Reid
BY Robb & Robb
ATTORNEYS United States Patent Office Plant Pat. 2,122
Patented Jan. 16, 1962

2,122
AZALEA PLANT

George Albert Reid, Linwood, N.J., assignor to Fischer Greenhouses, Linwood, N.J., a corporation of New Jersey Filed Dec. 20, 1960, Ser. No. 77,258
1 Claim. (Cl. 47—60)

The present invention relates to a new and distinct variety of azalea plant which was originated by me by crossing two unnamed and unpatented varieties on which no records of parentage were kept.

The primary objective of this breeding was to produce a new azalea variety which is winter-hardy and particularly suitable for the florist pot plant trade. This objective was fully achieved, along with other desirable improvements, as evidenced by the following unique combination of characteristics which are outstanding in my new variety and which distinguish it from its parents, as well as from all other varieties of which I am aware:

(1) Exceptionally good winter-hardiness, as evidenced by having withstood winter temperatures as low as −5° F., and even slightly lower, without injury, while growing in the fields under normal conditions and care;

(2) An ability to withstand full sun and moderate winds, with consequent usefulness for garden plantings, as well as for the florist trade;

(3) Large flower size:

(4) A frilled hose-in-hose flower form; and (5) A distinctive pink general color tonality of the flowers.

Asexual reproduction of my new variety by cuttings, as performed by me at Linwood, New Jersey, shows that the foregoing characteristics and distinctions come true to form and are established and transmitted through succeeding propagations.

The accompanying drawings shows typical specimens of the flowers of my new variety as depicted in color as nearly true as it is reasonably possible to make the same in a color illustration of this character.

The following is a detailed description of my new azalea variety, with color terminology in accordance with the Nickerson Color Fan, published by Munsell Color Company, Inc., of Baltimore, Maryland, except where general color terms of ordinary dictionary significance are obvious:

Locality where grown and observed: Linwood, New Jersey.

Propagation: Holds its distinguishing characteristics through succeeding propagations by cuttings.

*Plant*

Form: Bush; much-branched; compact.
Habit: Vigorous.
Rooting habit: Normal.
Foliage:
*Size.*—Large. Length—about 1½ inches. Width—about ¾ inch.
*Quantity.*—Normal.
*Color.*—New foliage: upper side—Moderate Yellow Green, Plate 5GY 5/6; under side—Brilliant Yellow Green, Plate 5GY 8/8. Old foliage: upper side—Moderate Olive Green, Plate 7.5GY 4/4; under side—Moderate Yellow Green, Plate 5GY 5/6.
*Shape.*—Oval pointed.
*Texture.* — Upper side — leathery. Under side — rough.

*Margin.*—Smooth edge.
*Aspect.*—Lush.
*Disease resistance.*—Good, as evidenced by the fact that no disease problems, including petal blight, have occurred over a period of several years, as compared with other varieties grown under the same cultural conditions in the same locality at Linwood, New Jersey.

*Flowers*

Borne: Several to stem; in regular rounded clusters; on strong stems of medium length.
Blooming habit: Uniform and profuse.
Blooming season: Normally commences about mid-May outdoors; excellent for forcing.
Quantity of bloom: Abundant, both outdoors and in greenhouse.
Continuity: One season.
Lasting quality: Excellent.
Size: Up to 2½ inches in diameter.
Petalage:
*Number of petals under normal conditions.*—10.
*Color.*—Ranging from Strong Purplish Pink, Plate 7.5RP 7/10 to Light Purplish Pink, Plate 7.5RP 8/5.
*Texture.*—Smooth.
*Appearance.*—Inside—center area of flower is slightly lighter in color than edge area. Outside—color is fairly uniform purplish pink.
*Shape.*—Petals are markedly waved or frilled.
*Arrangement.*—Two whorls of 5 petals each.
General color tonality: Clear pink.
Bud: Color—Strong Purplish Pink, Plate 7.5RP 7/10.

*Reproductive organs*

Stamens: Color—light pink.
Anthers: Color—dark brown.
Pollen: Color—white.
Styles: Color—pink.
Ovaries: Color—light pink.

*General observations*

The new variety combines the most desirable qualities of the Pericat type of azalea in respect to its flower size, form and color, with the hardiness of the Kaempferi or Kurume types. This combination is quite unique, and additionally so when these features are combined with good keeping qualities of the flowers under conditions of exposure to bright sun and moderate wind, which is the case in the present azalea variety, as evidenced by the fact that the flowers thereof remain fresh and erect, while other varieties wilt under the same conditions. The general flower form of my new variety is similar to the Pericat variety known as "Dawn" (unpatented), but the flower color is definitely darker than that of "Dawn" and more nearly like the flower color of the Pericat variety known as "Pink Supreme" (unpatented).

I claim:

A new and distinct variety of azalea plant, substantially as herein shown and described, characterized particularly as to novelty by the unique combination of exceptionally good winter-hardiness, the ability to withstand full sun and moderate winds, large flower size, a frilled hose-in-hose flower form, and a distinctive pink general color tonality of the flowers ranging from Strong Purplish Pink to Light Purplish Pink, with the center of the flower slightly lighter in color than the edge area.

No references cited.